United States Patent [19]

Oatley et al.

[11] Patent Number: 5,104,396
[45] Date of Patent: Apr. 14, 1992

[54] ABSORBENT PAD WITH HELICAL WICKING

[76] Inventors: John A. Oatley, 27 Franklin Cresent, Eastwood Hoe, Gonubie, Cape Province; David G. Levy, "Summerhill" Le Seuer Avenue, Constantia, both of South Africa

[21] Appl. No.: 301,911

[22] Filed: Jan. 25, 1989

Related U.S. Application Data

[63] Continuation of Ser. No. 83,550, Aug. 6, 1987, abandoned, which is a continuation of Ser. No. 902,342, Aug. 29, 1986, abandoned.

[30] Foreign Application Priority Data

Sep. 11, 1985 [ZA] South Africa ............ 85/6962

[51] Int. Cl.⁵ .............................. A61F 13/15
[52] U.S. Cl. .......................... 604/379; 604/380
[58] Field of Search ............ 604/378, 379, 380, 385.1, 604/327, 346, 358

[56] References Cited

U.S. PATENT DOCUMENTS

| | | | |
|---|---|---|---|
| 689,808 | 12/1901 | Johnson | 604/379 |
| 2,630,119 | 3/1953 | Aagesen | 604/379 |
| 2,891,544 | 6/1959 | London | 604/379 |
| 2,896,618 | 7/1959 | Schaefer | 604/378 |
| 3,356,090 | 12/1967 | Plantinga et al. | 604/385.1 |
| 3,442,268 | 5/1969 | Bird | 604/380 |
| 3,738,362 | 6/1973 | Sneider | 604/380 |
| 4,074,721 | 2/1978 | Smits | 604/380 |
| 4,205,679 | 6/1980 | Repke et al. | 604/379 |
| 4,425,128 | 1/1984 | Motomura | 604/385.1 |
| 4,850,481 | 3/1987 | O'Connor et al. | 604/380 |

FOREIGN PATENT DOCUMENTS 0885978  1/1962  United Kingdom ............ 604/378

Primary Examiner—John D. Yasko
Assistant Examiner—Anthony Gutowski

[57] ABSTRACT

This invention concerns an absorbent pad which is particularly useful for absorbing body fluids. The absorbent pad comprises a fluid-absorbent fibrous layer having a central portion and a peripheral portion, and a flexible fluid-pervious covering sheet for covering at least one side of the fibrous layer. A first wicking means is provided, conveniently by embossing, in the fibrous layer to conduct fluid outwardly from the central portion towards the peripheray of the fibrous layer. A second wicking means is in fluid conductivity with the first wicking means and conducts fluid from the first wicking means in a direction away from the first wicking means. Generally, the second wicking means conducts fluid around, but spaced from the periphery of the fibrous layer. A liquid-impervious, vapor permeable backing sheet can be provided. Helical or radial paths may be utilized for the wicking means.

4 Claims, 4 Drawing Sheets

ABSORBENT PAD WITH HELICAL WICKING

This is a continuation of application Ser. No. 06/083,550, filed Aug. 6, 1987, now abandoned, which is a continuation of Ser. No. 06/902,342, filed Aug. 29, 1986, now abandoned.

This invention relates to an absorbent pad especially for use in absorbing body fluids. The absorbent pad is capable of being used in an at least substantially upright position, and so is especially suitable as a breast pad for use by nursing mothers. It can also be used for absorbing other human fluids, e.g. as a diaper, incontinence pad, sanitary napkin, wound dressing, or the like.

BACKGROUND TO THE INVENTION

In the field of breast pads, we are aware of a specific type of absorbent pad for usa by nursing mothers. This type comprises a substantially circular pad having radial embossed lines in the form of spokes extending part way to the circumference. The radial embossed lines promote wicking of fluid from the center of the pad, (which would be against the nipple of a mother's breast), outwardly along the embossed lines of the pad. In use, those pads have not been found to be ideal because the force of gravity favors wicking downwards under gravity so that a pool of liquid is formed at the bottom edge of the pad, often resulting in leakage onto the mother's clothing.

Absorbent disposable pads for absorbing other body fluids are also well known. A very large number of inventions have been made and patents granted for disposable diapers, incontinence pads, sanitary napkins, wound dressings, and the like. In these items, there is typically an absorbent layer which usually forms the center of a sandwich construction having a flexible fluid-pervious covering sheet along at least one side. Sometimes there is a liquid-impervious flexible layer along one side of the absorbent layer.

Such pads are intended to be worn for a period of time during which they absorb the body fluid. Various proposals have been made for enabling the body fluid to be distributed over the pads, thereby to give them a longer period of use, make them less uncomfortable etc. Such proposals include providing areas of different absorptive power in the pad by embossing, densifying etc.

Although many proposals have been made, there is a need for an absorbent pad that can cause body fluid to travel from the point it is expelled from the human body onto the pad and then be distributed rapidly over a wide area of the pad, preferably without leaking from the periphery of the pad.

SUMMARY OF THE INVENTION

Accordingly the present invention provides an absorbent pad comprising a fluid-absorbent fibrous layer having a central portion and a peripheral portion, and a flexible fluid-pervious covering sheet for covering at least one side of the fibrous layer, a first wicking means in the fibrous layer adapted to conduct fluid outwardly from the central portion towards the periphery of the fibrous layer and a second wicking means in fluid conductivity in the fibrous layer with the first wicking means and adapted to conduct fluid from the first wicking means in a direction away from the first wicking means.

The pad can be used as a pad for absorption of human body fluids, e.g. for nursing mothers, as a wound dressing, an incontinence pad, as a diaper, as a sanitary napkin, or the like. The fibrous absorbent layer has at least the two wicking means. The first wicking means conducts fluid outwardly from the center of the layer towards, but short of, the edge of the pad. This first wicking means may extend outwardly along a plurality of lines. The second wicking means, and any further wicking means present, are in body liquid conductivity with the first wicking means for conducting body fluid in a direction away from the first wicking means e.g. in a path around but spaced from the edges of the absorbent layer.

Preferably the pad is a sandwich structure comprising a body liquid-impervious flexible backing sheet, the absorbent fibrous layer and the fluid-pervious covering or facing sheet. The backing sheet and the fluid pervious layer may be attached together around their peripheries, which conveniently can extend beyond the edges of the fibrous layer.

The liquid-impervious backing sheet is preferably substantially impervious to body exudates but is vapor-permeable. Examples of materials from which such sheets can be made are coated tissues and fabrics, perforated or microperforated films, foams, and melt blown fabrics of micro fibers. Such backing sheets reduce the occlusive nature of the pads, particularly when used as nursing pads, thereby reducing the risk of excessive skin hydration during use.

The invention particularly provides an absorbent article for a nursing mother, said absorbent article comprising a breast pad of a shape to be worn over a mothers breast, said pad comprising a sandwich structure of a liquid-impervious vapor-permeable backing sheet, a fibrous absorbent layer and a fluid-pervious flexible facing sheet, the fibrous absorbent layer being formed with a plurality of first wicking means extending outwardly from the center of the layer towards the periphery for conducting body fluid outwardly along a plurality of lines, and a second wicking means in fluid conductivity with the first wicking means for conducting body fluid in a direction away from the first wicking means.

The second wicking means may be formed by embossing, by forming a densified edge, or the like.

A sandwich structure of a flexible fluid-pervious sheet, an absorbent fibrous layer and a liquid-impervious vapor permeable backing sheet may be used for other types of absorbent pads referred to above. They can be made to a suitable shape for the intended use. Conveniently, a plurality of first wicking means extend outwardly from the central portion towards the periphery thereof. The backing sheet and the fluid-pervious sheet may be attached together, e.g. by plastics welding or adhesive material, around their peripheries when the peripheries extend beyond the periphery of the fibrous layer, or at any other convenient positions which ensure that the absorbent fibrous layer is held in position. The absorbent fibrous layer may be attached to either or both outer sheets in a similar fashion.

Various embodiments of the invention are possible. For example, the fibrous layer may have a plurality of first wicking means extending radially outwardly from the central portion towards the periphery thereof. Alternatively, the fibrous layer may have a first wicking means extending outwardly along a flattened helical path from the central portion towards the periphery thereof. The term "flattened helical path" means a path which starts from the central portion and continues as a continuous path with both curved and straight portions over a large distance towards the periphery without crossing itself, so that the appearance is as if a helix had been flattened in places to form the straight portions.

Preferably the second wicking means follows a path around the periphery of the absorbent layer but at a position between the central portion and the periphery. The first and second wicking means will hence form a continuous path.

If desired, the fibrous layer can have at least one further wicking means between the second wicking means and the periphery of the layer, said at least one further wicking means being in fluid conductivity with the second wicking means and adapted to conduct fluid in a direction away from the second wicking means. At least two further wicking means can be provided, the further wicking means then being in fluid conductivity with each other, and arranged to conduct the fluid successively from the second wicking means towards the periphery of the pad.

In one embodiment, a third wicking means in fluid conductivity with the second wicking means and adapted to conduct fluid outwardly from the second liquid means, may be provided. In this embodiment the fibrous layer conveniently also has a fourth wicking means in fluid conductivity with the third wicking means and adapted to conduct fluid in a direction away from the third wicking means. The fourth wicking means may extend in a direction around the periphery but at a position between the third wicking means and the periphery.

Conveniently, the first wicking means can comprise one or more embossed lines extending from the center of the fibrous absorbent layer towards the periphery of the pad. The lines may terminate shortly before the edge of the absorbent layer. For one embodiment of breast pad there may be about three lines at angles of from 100 to 130° to each other. The center of the absorbent layer may also have an embossed indentation adapted for conveniently fitting over the nipple of the nursing mother's breast. This indentation (when present) is preferably in liquid conductivity with the first wicking means so that it constitutes part of the first wicking means. It is to be understood that, if desired, more than one absorbent layer may be present.

The second wicking means can be an embossed line or lines extending around but spaced from the periphery of the pad. The line or lines may extend completely around the periphery or may extend part way around a sector (clockwise and/or anti clockwise) between adjacent radial first wicking lines. Conveniently there may be a single embossed second wicking line closely adjacent to the periphery of the fibrous absorbent layer and extending completely around the periphery of that layer.

For a nursing pad, the facing side of the absorbent layer may resemble a spoked wheel. There may, for example, be three spokes but further numbers of spokes can exist is desired. The spokes conveniently may extend to about 5 mm from the periphery of the absorbent layer. Consequently, the circular second wicking means can be at a radius from the center to provide approximately a 5 mm gap between it and the periphery of the absorbent layer.

In a second embodiment of the nursing pad, the fibrous absorbent layer can again have a central embossed indentation to receive the nipple of the nursing mother's breast and can have spokes extending outwardly therefrom. As mentioned hereinbefore, the indentation, when present, constitutes part of the first wicking means. However, in this embodiment, the exterior ends of the spokes do not lead to an embossed circumferential channel but to a densified edge at the periphery of the absorbent layer. The spokes may terminate at the start of the densified edge or may end completely at the circumference of the absorbent layer. The densified (or crushed) edge may have a bulk density of at least about ten times that of the least dense portion of the absorbent layer. There may be a gradually increasing density gradient to the edge of the layer. The nursing pads conveniently are substantially circular in plan view.

The densified edge may be made by crush-cutting of the absorbent layer. The densified edge is such that fluid reaching it is rapidly transported in a direction extending away from the radial channels embossed on the absorbent layer. The fluid conveniently is transported in a circumferential direction by the densified edge away from the radial spokes.

The absorbent layer itself can be any suitable pad of an absorbent material. It may be a single layer or a plurality of layers of suitable thickness. It may be made of absorbent cellulose, such as defibrillated wood fibers, tissue wadding or the like, or a combination of suitable materials. The purpose of the absorbent layer is to absorb the fluid which reaches the center of it.

Defibrillated wood fibers can comprise coarse or fine fiber pulps typical of softwoods and hardwoods, respectively, or mixtures thereof. These pulps can be produced by any conventional pulping and/or bleaching process and may additionally be treated with surface active agents to improve softness, to aid defibrillation or to promote the formation of permanent densified layers or regions in the pad. If desired, skin-forming agents, such as water or polyvinyl acetate may be used to treat absorbent cellulose to promote absorption over as great an area as possible. They also make the embossed wicking means more permanent.

The wicking means for conducting the liquid from the center and around the edges of the absorbent layer may be formed by any standard embossing means. Similarly, where densification is effected, this may be by any suitable crush cutting, pressing or the like, of the absorbent layer.

The flexible liquid-impervious backing sheet, when present, can be any suitable liquid-impermeable backing sheet. Particular examples are vapor permeable polymeric films. If desired such a backing sheet may be backed by a further layer, e.g. a non-woven fabric.

The flexible fluid-pervious facing sheet can be any suitable such sheet which will permit the body fluid to pass through it. A polypropylene non-woven fabric is particularly convenient to use. The facing sheet and backing sheet may be joined together around the edges in any convenient manner, e.g. by heat-sealing, adhesive or the like. Additional backing layers may be attached in any suitable manner. The additional backing layers, when present, may provide a non-slip surface or act as a substrate for an adhesive attachment means. The adhesive attachment means for a breast pad may, for example, involve one or more strips from which a cover film may be removed to reveal an adhesive surface for attachment to the interior of the mother's brassiere For other uses other attachment means may be provided, e.g. securing tabs for an diaper or incontinence pad.

In the case of a breast pad, the embossing is such that the portion adapted to fit over the nipple conveniently is central in a circular breast pad. However, other shapes can be used. Furthermore, the point from which the wicking lines extend outwardly need not be at the exact center.

The wicking lines conveniently extend outwardly in several directions. In use, for breast pads, the pads can be positioned in any radial position including the position where there is a vertical wicking line extending from the center downwardly. The pads may, however, be marked to show a top point and have wicking lines extending outwardly with the nearest passages to the bottom point being at about 60° to the vertical. Even if a pad does have a vertical downwardly extending passage, it has been found that the fluid, after wicking towards the edge continues wicking around the second wicking means away from the bottom edge. The continuance of wicking around the edge of the pad means that fluid is continually drawn away from the central area of impingement, towards the edge and around the edge. This reduces the possibility of stains to the clothes of the mother by leakage at the bottom and also enables the breast pad to be used for a reasonable length of time.

As indicated above, the absorbent pad may be utilized as a wound dressing, a diaper an incontinence pad or other suitable pad for absorption of human fluids. The invention further provides such products comprising a pad in accordance with the invention. The shapes of such pads and consequently the products themselves can be varied to suit the particular use to which the pads are to be put. Pads suitable as wound dressings may be made with or without the liquid-impervious flexible backing sheet, dependant on whether containment of wound exudate is desired or transport of exudates to a secondary layer is desired.

BRIEF DESCRIPTION OF THE DRAWINGS

The invention is illustrated in non-limiting manner by reference to the accompanying drawings in which.

DETAILED DESCRIPTION

Figure 1:
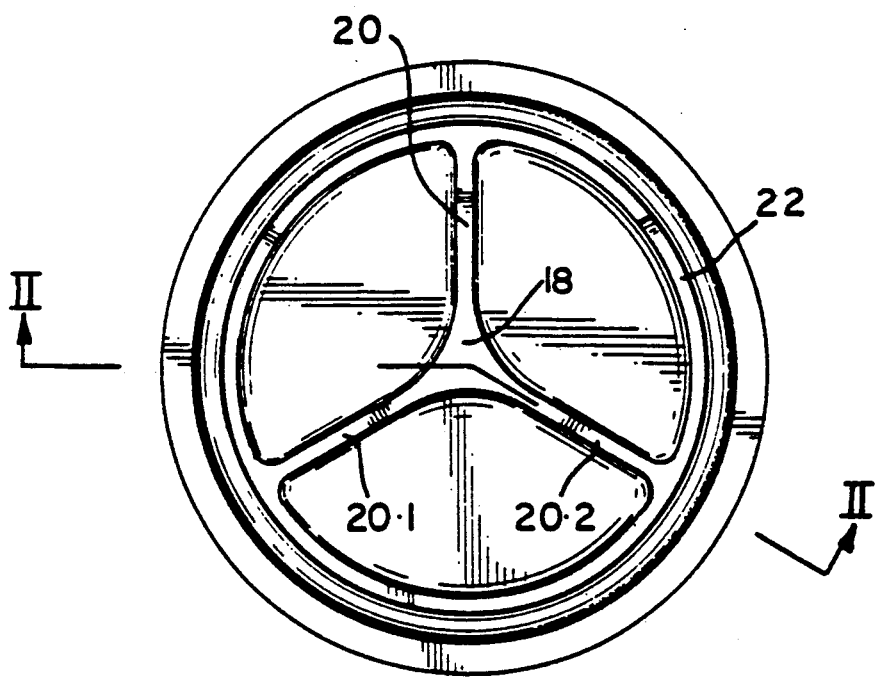
FIG. 1 is a plan view of a first embodiment of a nursing mother's absorbent pad in accordance with the invention.
Figure 2:
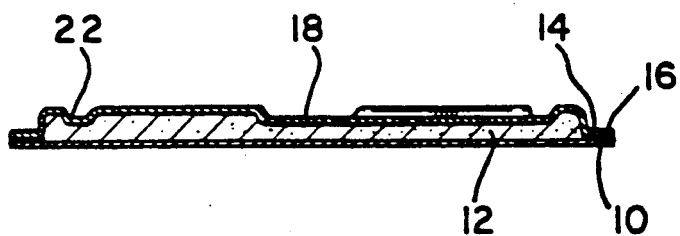
FIG. 2 is a cross section through II—II of FIG. 1.

In FIGS. 1 and 2 a breast pad for a nursing mother has a liquid-impervious vapor-permeable backing sheet 10 of cellulose tissue treated with a repellent agent such as AQUAPEL 360XC (trade name) from Hercules Company, with an absorbent layer in the form of a pad 12 positioned on it. The pad 12 is sandwiched between the sheet 10 and a liquid-pervious sheet 14 of polypropylene non woven fabric. The sheets 10 and 14 are attached together by heat sealing around their periphery 16.

Before or after adhering the sheets 10 and 14 together, embossing is carried out to form the embossed shape shown in FIG. 1. Thus there will be first wicking means comprising a central indentation 18 and three radial indentations 20, 20.1 and 20.2 radially spaced at 120°, and a second wicking means in the form of a circumferential indentation 22, joining the ends of the radial indentations to form a three spoked wheel pattern.

In use, the indentations 18, 20 and 22 enable fluid to be led to and around the outer peripheral portion of the absorbent layer.

Figure 3:
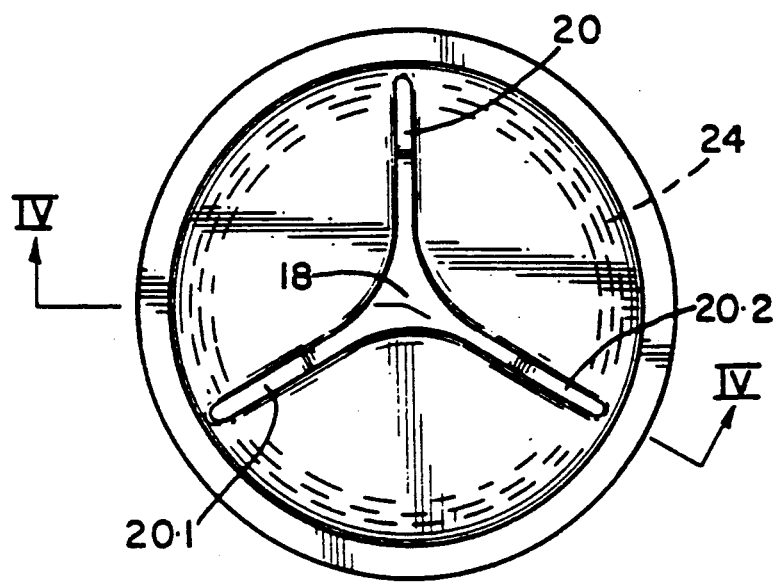
FIG. 3 is a plan view of a second embodiment of a nursing mother's absorbent pad in accordance with the invention.
Figure 4:
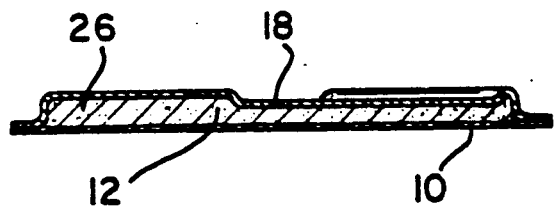
FIG. 4 is a cross section through IV—IV of FIG. 3.

Referring now to FIGS. 3 and 4, the periphery of the pad is densified by means of crush cutting at 24 to form second wicking means in the form of a densified edge 26. Embossing is also carried out to provide the first wicking means, i.e. the central indentation 18 and the channels 20, 20.1 and 20.2. The crush cutting forms a densified edge 26 extending from one arm of the channel (e.g. 20) to the next arm (e.g. 20.2).

In use, the body fluid from the mothers nipple, reaching the center of the pad is conducted from the indentation 18 along the channels 20 and then via the densified edge 26 around the circumference of the pad. Excellent absorbency and dispersion of the fluid from the center portion to the circumference is obtained.

Figure 5:
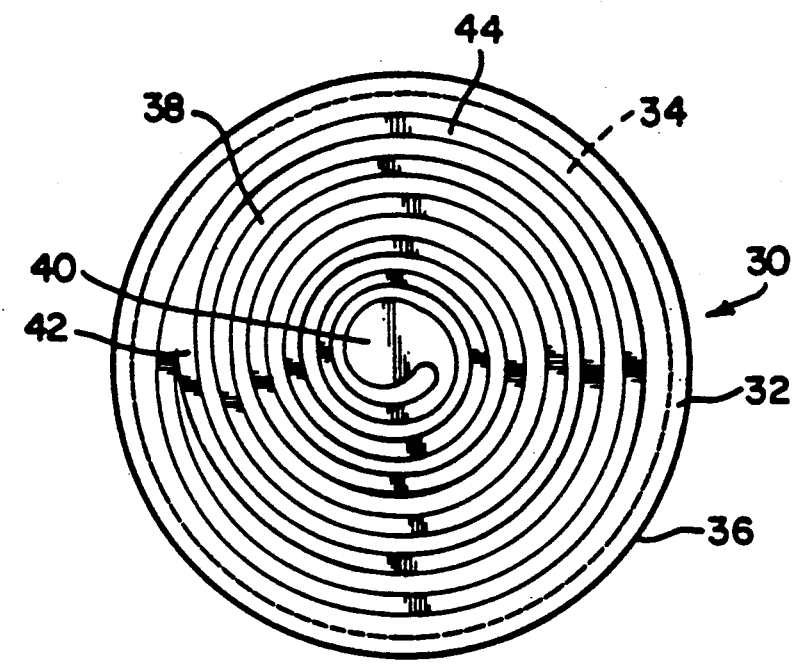
FIG. 5 and 6 are plan views of third and fourth embodiments of a nursing mother's absorbent pad in accordance with the invention.

In FIG. 5, a pad shown generally at 30 comprises a fluid-pervious covering sheet 32 and beneath which is a flexible absorbent fibrous layer 34. The sheet 32 is attached around its periphery 36 to a backing sheet (not visible) beneath the fibrous layer. By means of embossing, a first wicking means is provided. The first wicking means comprises a helical path 38 extending from central indentation 40 outwardly towards the periphery 36. The first wicking means ends at the end of the helix 42 and a second, and substantially circular, wicking means 44 leads from the first wicking means. The second wicking means is also formed by embossing. In use, fluid moves through a helical path along the first wicking means from the center 40 until it reaches the second wicking means at 42, when it is moved away from the first wicking means around the periphery of the absorbent layer 34 but not closely adjacent to the periphery of the pad 30. In this way, the fluid is directed over substantially all of the area of the absorbent layer 34.

In the embodiment illustrated in FIG. 5, we have found that a pad conveniently can be made with a helical spiral having approximately 3 mm between adjacent paths and with the embossed paths about 3 mm wide. Conveniently, the overall radius is approximately 38 mm and the nipple indentation conveniently may have a radius of about 8 mm.

Figure 6:
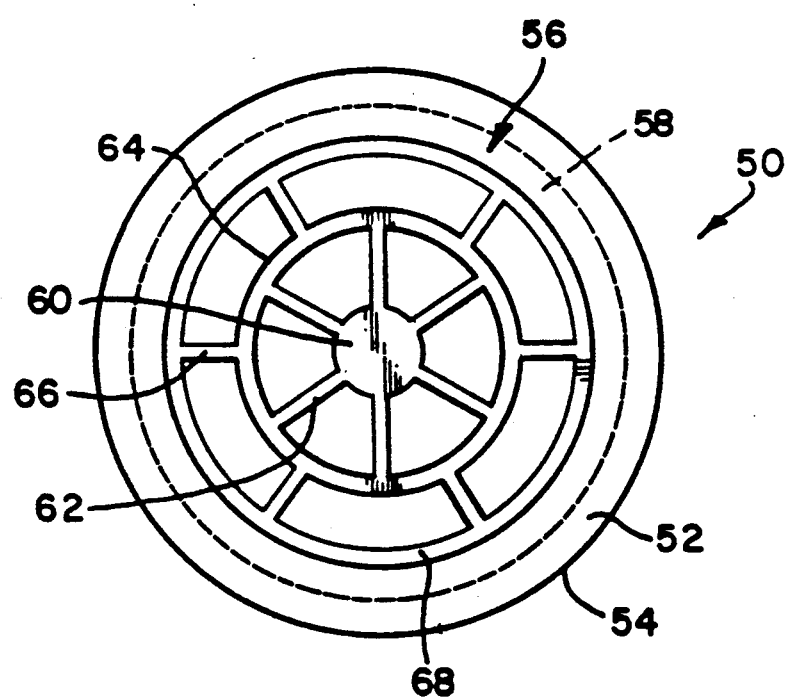

In FIG. 6, a nursing mother's pad shown generally at 50 has a fluid-pervious covering sheet 2 attached around its periphery 54 to a liquid-impervious vapor-permeable backing sheet (not visible). A pattern shown generally at 56 is embossed onto a fibrous layer 58. The pattern 56 comprises a central indentation 60 in fluid connection with a plurality of spokes 62, the central indentation and spokes together forming the first wicking means. These spokes 62 extend radially outwardly to a circular second wicking means 64. Radial lines 66 extend outwardly from the second wicking means 64 and act as a third wicking means. The third wicking means extends as far as a circular embossed fourth wicking means 68 spaced away from the periphery 54 of the pad 50.

The embodiment of FIG. 6, in use, receives fluid from the mother's nipple onto the central embossed indentation 60. The fluid passes outwardly along the radial spokes 62 and then around the second wicking means 64. Although much of the fluid is absorbed, excess fluid can pass along the third wicking means 66 radially outwardly to the fourth wicking means 68. In following these embossed indentations, the fluid is spread in a controlled manner over a substantial area of the absorbent layer 58.

In still further embodiments (not shown), yet further wicking means, similar to the third and fourth wicking means, and in fluid conductivity with the fourth wicking means can be provided, these further wicking means then being located between the fourth wicking means and the periphery 54 of the pad 50.

Figure 7:
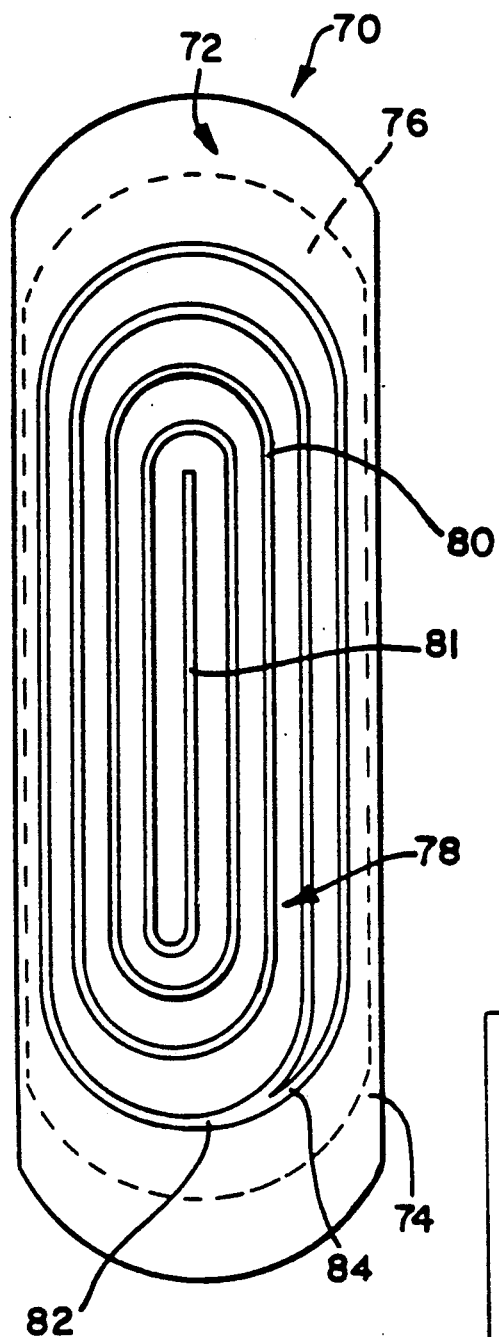
FIG. 7 is a plan view of a sanitary pad in accordance with the invention.

Referring now to FIG. 7, a sanitary pad is shown generally at 70. It has a fluid-pervious cover sheet 72 attached around its periphery 74 to a liquid-impervious flexible backing sheet (not visible). A fibrous layer capable of absorbing body fluid is shown at 76. The fibrous layer has an embossed pattern of wicking means shown generally at 78 formed on it. First wicking means 80 extends from the center (81) of the fibrous layer 76 by means of a flattened helical path. It terminates at point 82 where second wicking means 84, extending around the periphery of the fibrous layer 76 (but spaced inwardly therefrom) is positioned. The first and second wicking means 80 and 84 are in fluid communication with each other.

Figure 8:
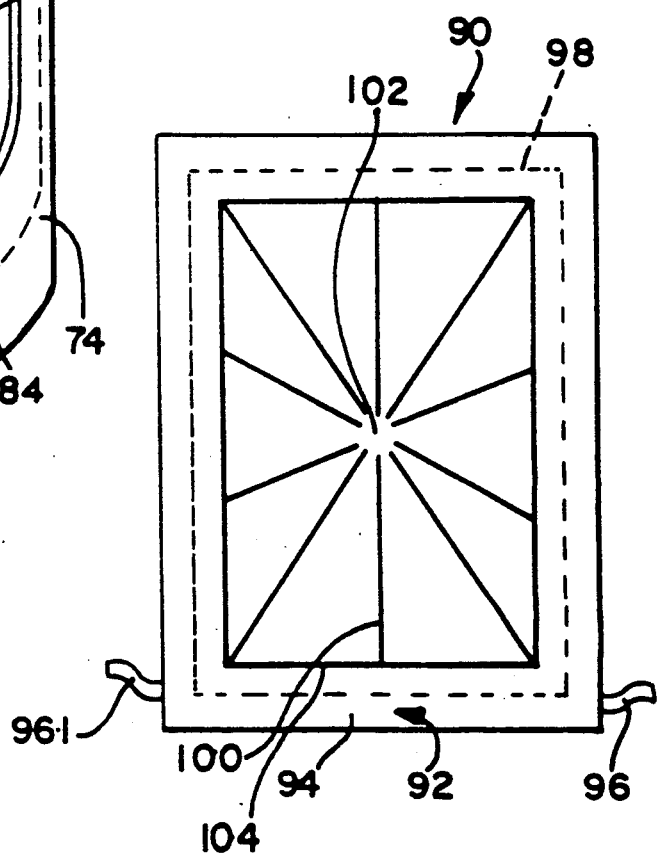
FIG. 8 is a plan view of a diaper/incontinence pad in accordance with the invention.

The embodiment illustrated in FIG. 8 is of a diaper-/incontinence pad shown generally at 90. The pad 90 has a fluid-pervious covering sheet 92 attached around its periphery 94 to a backing sheet (not visible). Securing tabs 96, 96.1 are fixedly attached to the backing sheet. A fluid-absorbent fibrous layer 98 is positioned within the sandwich formed by the fluid-pervious covering sheet and the backing layer. The fibrous layer 98 has a first wicking means 100 extending outwardly from the center 102 of the fibrous pad to a second wicking means 104 which is positioned away from the edge of the fibrous layer.

In use, all of the embodiments of the invention enable body fluid to be moved along the first wicking means to the second wicking means, being partially absorbed on the way.

In order to test the embodiments of the invention, a breast mold was molded to the shape of a woman's breast with approximately a 1 mm nipple and an overall maximum diameter of about 190 mm and distance of the nipple from the back of the breast of about 46 mm. Colored liquid, at a constant flow rate was applied to a test pad through the breast mold to which the pad was attached. The colored liquid was rhodamine red dye as a 1% solution in water.

The procedure used was to set the flow rate to 20 ml per hour and to weigh the test pad before the test. After placing the pad over the nipple and securing it thereto, flow of liquid was started. The flow of liquid was stopped once the pad failed. Failure was determined once the red dye reached a transparent plastic wrap positioned behind the pad, failure being generally at the bottom edge of the pad. The pad was then weighed again. Thereafter the mass of liquid which was absorbed by the pad was obtained by subtracting the second weight from the first weight. By observing the fluid wicking and absorbency of the embossing lines, and comparing the results, it was possible to determine the absorbency capacities of the pads and to show that the pads of the invention had a high distribution of fluid into the pulp. A number of experiments were carried out, which are set forth below.

EXPERIMENT 1

Two pads in accordance with FIG. 3 were compared. One pad was of 90 mm diameter size and contained 26% more absorbent pulp than a smaller pad of 80 mm size. However, the larger pad was only 10% more absorbent. This means that, on a mass by mass basis, the smaller pad was 15% more absorbent. In the larger pad the first wicking means terminated well away from the second wicking means whilst in the smaller pad the first wicking means terminated within the densified edge which comprised said second liquid reaching the second wicking means continued around the edge in a better manner than with the larger pad where gravity had a substantial effect.

EXPERIMENT 2

Experiment no 1 was repeated with a further larger prototype but with the embodiment of FIG. 1. Absorbency tests showed that the provision of the second wicking means, compared with a standard pad for which no second wicking means was provided, caused an increased absorbency of 27%.

EXPERIMENT 3

A further pad of example 1 was compared with a commercially available sample of a nursing pad comprising defibrillated pulp filler backed by an impervious sheet and faced with a non-woven fabric. It was ovate in shape and had two parallel sides and two convexly rounded ends. The pulp of the comparison pad had eight radial lines extending outwardly from the center starting 6 mm from the center and ending 12 mm from the edge of the pulp pad. There was no second wicking means. The absorbency capacity of the commercial pad was found to vary depending on the radial position of the lines. It failed after absorbing from 2,5 grams to 3,6 grams of liquid depending on whether or not the wicking lines were disposed vertically downwardly.

Contrary thereto, the pad of the invention absorbed 3,9 grams of liquid with a radial line pointing vertically downwards (the worst theoretical position) and also 3.9 grams of liquid with a radial line pointing vertically upward (the best theoretical position).

EXPERIMENT 4

Various embossing patterns using the pad according to the invention were compared. The pads were tested for absorbency and compared with a standard which was not embossed. Each of the embossed pads had the first wicking means in the form of spokes extending in a rim as the second wicking means. The results were as follows:

| | | |
|---|---|---|
| Without embossing | 1,50 g ± 0,20 g | absorbed |
| Three spoked wheel | 1,82 g ± 0,19 g | (21% increase) |
| Five spoked wheel | 2,10 g ± 0,5 g | (40% increase) |
| Eight spoked wheel | 2,45 g ± 0,32 g | (63% increase) |

EXPERIMENT 5

An experiment was carried out to compare pads of the invention with an eight spoked wheel design and with a sixteen spoked wheel design, each with a circumference. The samples comprised defibrillated pulp and had a non-woven fabric facing but no liquid-impervious backing. The sixteen spoked wheel provided 50% densification by area and a liquid travel distance of 720 mm whereas the eight spoked wheel provided a 35% densification by area and a liquid travel distance of 416 mm. The results were:

| | | |
|---|---|---|
| Eight spoked wheel design | 2,08 g ± 0,75 g | absorbed |
| Sixteen spoked wheel design | 2,45 ± 0,9 g | absorbed |

EXPERIMENT 6

To determine the effect of embossing pressure on the functioning of the wicking means, an eight spoked wheel design according to the invention and comprising a facing layer and a defibrillated absorbent layer but with no backing layer was embossed at various pressures. The results were as follows:

| Embossing pressure | Absorbency capacity |
|---|---|
| 285 p.s.i. | 2,08 ± 0,75 g |
| 457 p.s.i. | 2,11 ± 0,25 g |
| 571 p.s.i. | 2,26 ± 0,42 g |
| 799 p.s.i. | 2,35 ± 0,22 g |
| 1028 p.s.i. | 3,02 ± 0,56 g |

EXPERIMENT 7

It was found that a longer embossing time improved absorbency capacity as demonstrated by the following results from an eight spoked wheel design according to the invention.

| Embossing time | Absorbency capacity |
|---|---|
| 1 second | 2,08 ± 0,75 g |
| 15 seconds | 2,51 ± 0,19 g |

EXPERIMENT 8

To determine the amount of milk absorbed in nursing pads when worn by nursing mothers, 320 pads of various designs were worn by preselected nursing (and leaking) mothers. 284 of the pads were returned and weighed to determine the mass of milk absorbed. The results of these tests on the prior art pads showed that in 90% of cases, the mass of milk absorbed was less than 3 grams. In only 5% of cases was the mass absorbed greater than 6 grams.

EXPERIMENT 9

As a comparison with experiment 8, pads in accordance with FIG. 1 and of 80 mm diameter were worn by selected nursing (and leaking) mothers. Although this involved only a limited number of pads, the results were as follows:

TABLE A

| | Time worn | | |
|---|---|---|---|
| | 4 hours | 4 to 8 hours | 8 hours |
| Number of pads worn | 5 | 22 | 6 |

TABLE B

| Milk absorbed | 0-1 | 1-2 | 2-3 | 3-4 | 4-5 | 5-6 | 6-7 | more than 7 g |
|---|---|---|---|---|---|---|---|---|
| (g) Number of pads | 19 | 6 | 3 | 0 | 2 | 0 | 1* | 2* |

*samples leaked to some extent

The mass increase recorded for the three pads which eventually leaked were 9,5 g, 8,26 g and 6,44 g. This indicates that the pads will be effective in 95% of the cases.

As can be seen from the invention, a high percentage of densified area is available for absorption. Further, a substantial distance can be provided on the pads of the invention through which the fluid must travel before reaching the failure zone (final edge) of the fibrous absorbent layer. Furthermore, the method of enabling wicking to take place according to the invention causes the fluid to move, even against gravity.

If the wicking means is applied by embossing, this stabilizes the defibrillated pulp of the absorbent fibrous layer so that the product resists breaking apart under the influence of body movement. Without embossing, this would be particularly likely with hardwood fibers because these fibers are short and fine and do not intermesh to form a stable batt, as do long coarse fibers of softwood pulps.

We claim:

1. An absorbent pad comprising a fluid-absorbent fibrous layer having a central portion, a periphery and a peripheral portion adjacent said periphery, a flexible fluid-pervious covering sheet covering at least one side of the fibrous layer, a first wicking means comprising at least one outwardly extending embossed indentation in the fibrous layer, said first wicking means being adapted to conduct fluid outwardly from the central portion toward the periphery of the fibrous layer and a second wicking means in the fibrous layer, said second wicking means comprising an embossed indentation located inwardly of said periphery, said second wicking means being adapted to conduct fluid received from the first wicking means along a path in said peripheral portion, said path being parallel to said periphery, said outwardly extending embossed indentation comprising said first wicking means being in the form of a helix.

2. An absorbent pad according to claim 1 wherein said outwardly extending, helical form embossed indentation has a first end and a second end, said first wicking means further comprises a centrally located embossed indentation and said second wicking means comprises an uninterrupted embossed indentation which follows a path extending completely around but spaced inwardly from the periphery of said fibrous layer, the first end of said helical-form embossed indentation being joined to said second wicking means and the second end of said helical-form embossed indentation being joined to said centrally located embossed indentation.

3. An absorbent pad comprising a fluid-absorbent fibrous layer having a central portion, a periphery and a peripheral portion adjacent said periphery, a flexible fluid-pervious covering sheet covering at least one side of the fibrous layer, a first wicking means comprising at least one outwardly extending embossed indentation in the fibrous layer, said first wicking means being adapted to conduct fluid outwardly from the central portion toward the periphery of the fibrous layer and a second wicking means in the fibrous layer, said second wicking means comprising an embossed indentation located inwardly of said periphery, said second wicking means being adapted to conduct fluid received from the first wicking means along a path in said peripheral portion, said path being parallel to said periphery, said outwardly extending embossed indentation comprising said first wicking means being in the form of a flattened helix.

4. An absorbent pad according to claim 3 wherein said outwardly extending, flattened helical form embossed indentation has a first end and a second end, said first wicking means further comprises a centrally located embossed indentation and said second wicking means comprises an uninterrupted embossed indentation which follows a path extending completely around but spaced inwardly from the periphery of said fibrous layer, the first end of said flattened helical-form embossed indentation being joined to said second wicking means and the second end of said flattened helical-form embossed indentation being joined to said centrally located embossed indentation.

* * * * *